(12) United States Patent
Fromherz et al.

(10) Patent No.: US 7,326,539 B2
(45) Date of Patent: Feb. 5, 2008

(54) MEASUREMENT DEVICE AND METHOD FOR SCREENING WITH CELLS IMMOBILIZED ON ELECTRODES

(75) Inventors: Peter Fromherz, Munich (DE); Matthias Brittinger, Wessling (DE)

(73) Assignee: Max-Planck-Gesellschaft zur Foerderung der Wissenschaften e.V., Müenchen (DE)

( * ) Notice: Subject to any disclaimer, the term of this patent is extended or adjusted under 35 U.S.C. 154(b) by 381 days.

(21) Appl. No.: 10/666,530

(22) Filed: Sep. 22, 2003

(65) Prior Publication Data

US 2005/0037438 A1   Feb. 17, 2005

(30) Foreign Application Priority Data

Sep. 19, 2002   (DE) ................ 102 43 599

(51) Int. Cl.
  *G01N 33/53*   (2006.01)
  *G01N 33/566*   (2006.01)
(52) U.S. Cl. .................. 435/7.2; 436/501
(58) Field of Classification Search ............ 435/7.2, 435/501
  See application file for complete search history.

(56) References Cited

U.S. PATENT DOCUMENTS 5,827,655 A   10/1998   Chandy et al.
6,051,442 A   4/2000    Kuroda
6,602,399 B1 *   8/2003   Fromherz et al. ........ 205/777.5
2002/0086298 A1   7/2002   Lester
2002/0168625 A1 *   11/2002   Weaver ................ 435/4

FOREIGN PATENT DOCUMENTS

WO   WO/01/70002   * 9/2001
WO   WO 01 70002 A   9/2001
WO   WO 01 94375 A1   12/2001

OTHER PUBLICATIONS

Meme et al. Low Sodium is Accompanied by Diastolic CA2+ Gain and Systolic Loss in Solated Guinea-Pig Ventricular Myocytes; Journal of Physiology, vol. 530, No. 3 (2001) pp. 487-495.*
Plugge et al. A Potassium Channel Protein Encoded by Chlorella Virus PBCV-1; Science, vol. 287 (2000) pp. 1641-1644.*
Baumann et al., "Microelectronic sensor system for microphysiological application on living cells", Sensors and Actuators B, vol. 55, No. 1, Apr. 25, 1999, pp. 77-89.

* cited by examiner

*Primary Examiner*—Jon Weber
*Assistant Examiner*—Paul Martin
(74) *Attorney, Agent, or Firm*—Rothwell, Figg, Ernst & Manbeck (57) ABSTRACT

The present invention relates to a method and a device for screening with cells immobilized on electrodes by using a low-salt medium. In particular, a method is disclosed for determining whether a substance is a modulator of a target component in a cell immobilized on an electrode.

6 Claims, 9 Drawing Sheets

MEASUREMENT DEVICE AND METHOD FOR SCREENING WITH CELLS IMMOBILIZED ON ELECTRODES

The present invention relates to a method and a device for screening with cells immobilized on electrodes by using a low-salt medium. In particular, a method is disclosed for determining whether a substance is a modulator of a target component in a cell immobilized on an electrode.

BACKGROUND OF THE INVENTION

So-called cellular screening methods are often used to determine pharmaceutical effects of test substances. In these, living cells are brought in contact with the test substances in order to determine the function of the latter as possible effectors on target components in a cell, for example receptors and/or ion channels. To this end, International Patent Application PCT/EP01/03209 proposes the use of a system in which the effect of a test substance on the activity of a cell is measured by a field-effect transistor placed underneath it.

BRIEF SUMMARY OF THE INVENTION

Measurements of analytes by using living cells immobilized on chips are also described in WO 96/31774, U.S. Pat. No. 6,051,422, Baumann et al. (Sensors and Activators B55 (1999), 77 –89) and Fertig et al, (Biophys. J. 82 (2002), 3056 –3062). A problem with such measuring instruments, however, is that often only a small measurement signal is obtained at the electrode in contact with the cell. It is therefore an object of the invention to provide an improvement to known measuring instruments and measurement methods, by which, on the one hand, the measurement signal is increased and, on the other hand, a new measurement method is made possible with cells immobilized on electrodes.

This object is achieved in that the measurement is carried out in a medium which has an increased electrolyte resistance. The signal-to-noise ratio during the measurement can then be improved by a factor of up to 5 or more. The medium which is used has a salt concentration of $\leq 100$ mmol/l, particularly preferably $\leq 50$ mmol/l, and most preferably $\leq 20$ mmol/l (expressed as total concentration of the cations present in the medium, especially alkali metal and alkaline-earth metal cations). The minimum salt concentration is preferably $\geq 1$ mmol/l and particularly preferably $\geq 2$ mmol/l. The measurement medium is furthermore essentially free of sodium ions, i.e. it has a sodium ion concentration of $\leq 10$ mmol/l, particularly preferably $\leq 5$ mmol/l, and most preferably $\leq 1$ mmol/l. The use of a measurement medium entirely free of sodium ions is more particularly preferred for measurements on potassium-selective ion channels. The use of a sodium-free medium is also particularly preferred for measurements on chloride-selective or non-specific ion channels.

The osmolality of the measurement medium may optionally be increased by adding non-ionic substances, for example carbohydrates, and adjusted to a range of between 250–400 Osm, particularly preferably 290–360 Osm. The carbohydrate concentration in the measurement medium is preferably 280–340 mM.

The measurement is preferably carried out as a current, potential or/and voltage measurement on the gap between the electrode and the cell irmaobilized on it. When a medium according to the invention is used, the conductance in the gap has a value of about 10–50 mS/cm$^2$, whereas values of 200–1000 mS/cm$^2$ are encountered according to the prior art.

The measurement method is preferably carried out with individual cells on a potential-sensitive electrode.

A first aspect of the present invention relates to the use of the low-salt measurement medium in a cellular screening method, i.e. in a method for determining whether a substance is a modulator of a target component in a cell. Such a method preferably comprises the steps of:
(a) preparing a cell, which contains the target component, immobilized on an extracellular potential-sensitive electrode,
(b) bringing a substance to be tested in contact with the cell, in a medium which has a salt concentration of $\leq 100$ mmol/l,
(c) measuring a signal at the electrode due to the target component, and
(d) determining the effect of the substance to be tested on the measurement signal.

The method according to the invention is suitable for determining the effect of test substances on any target components in the cell, provided that the target component can give rise to a measurable signal at the electrode, or a change in a measurable signal at the electrode. The determination preferably addresses whether a substance is a modulator of a membrane-associated target component.

The target component may preferably comprise one or more polypeptides. In a particularly preferred embodiment, the target component comprises an ion-channel/receptor system comprising an ion-channel component, i.e. one or more polypeptides which can mediate ion transfer through a cell membrane, i.e. transfer of cations and/or anions. The ion-channel/receptor system furthermore comprises a receptor component which can react to a stimulus. This receptor may be the ion channel or a part of the ion channel. The receptor, however, may also be a molecule which is different from the ion channel but which is operatively connected with the ion channel, i.e. a change in the function and/or conformation status of the receptor leads to a variation in the function status of the ion channel, so as to cause a detectable change in the ion current through the cell membrane. The stimulation of the receptor is preferably carried out by changes in the potential (inside or outside the cell), by the presence or absence of effectors, by illumination, by mechanical stimulation or combinations thereof. Particularly preferred examples of target components are voltage-controlled, ligand-controlled and mechanically controlled ion channels such as potassium channels, for example the human potassium channels hSlo and KV 1.3. Other preferred examples of membrane-associated target components are receptors, especially NMDA, GABA, AMPA or acetylcholine receptors.

The measurement of the method according to the invention is carried out on a living cell. The cell may be a micro-organism, for example a bacterial cell or a yeast or fungal cell. The cell, however, is preferably a eukaryotic cell, particularly preferably a mammalian cell, for example a human cell. The cell preferably has a diameter of $\leq 50$ µm.

It is furthermore preferable for the cell to over-express one or more polypeptides which form the target component or a part thereof and/or which increase the activity of the target component. Such a cell may, for example, be obtained by recombinant methods or mutations and exhibits a higher activity of the target component than a comparable untreated cell. The cell is particularly preferably transfected with nucleic acid molecules which code for the cell component. In this embodiment, the cell comprises heterologous nucleic acid molecules which code at least part of the target component and which allow over-expression of this component.

A preferred embodiment of the method according to the invention comprises the use of transgenic cells which are transfected with nucleic acids coding for the α and/or β units of the voltage-dependent potassium channel hSlo or for the voltage-dependent potassium channel KV1.3. Another preferred embodiment of the invention comprises the use of cells which are transfected with nucleic acids coding for the NMDA receptor, the AMPA receptor or the GABA receptor, or an acetylcholine receptor.

The cell is cultivated on a potential-sensitive electrode, especially on a planar potential-sensitive electrode. Methods for this are described, for example, by Vassanelli and Fromherz (Appl. Phys. A 65 (1997), 85–88). In this way, it is possible to obtain cells which grow on the potential-sensitive region of an electrode, which results in operative contact between the cell and the electrode.

The electrode surface on which the cell is immobilized may be silicon oxide, another semiconductor or a metal. The electrode may be integrated on a chip, the chip preferably containing a transistor. The chip particularly preferably has at least one integrated field-effect transistor, which contains a source and a drain. The potential-sensitive electrode, however, may also be a metal electrode integrated on a chip. A transistor or the electrode is preferably covered fully by the adhesion surface of the cell.

In a preferred embodiment of the method according to the invention, an array is provided which comprises a multiplicity of cells immobilized on respectively different extracellular potential-sensitive electrodes. Such an array with, for example 10 or more, especially 50 or more cells may be used for high-throughput screening, a multiplicity of test substances being determined in parallel.

The functional characteristics of the target component in the cell comprise the creation of a measurable signal at the electrode. If the target component is an ion channel, for example, opening it causes an ion current to flow out of the cell or/and into the cell. This ion current also flows in the vicinity of the operative contact between the cell and the electrode, giving rise to a detectable signal which can be measured by the extracellular potential-sensitive electrode. The detectable signal may, for example, be a voltage drop in the gap between the cell and the electrode or the change in the surface potential of the electrode due to diffuse ion concentration changes in the operative contact region.

A change in the functional characteristics of the target component, for example the conductance of the ion channel, leads to a change in the ion current and therefore in the electrical signal which can be detected by the electrode. The presence of a modulator of the target component also leads to a change in its functional characteristics compared with a control determination in the absence of the modulator. If the ion channel reacts to a modulator, for example, this leads to a change in the ion current and therefore to a detectable signal change.

The method according to the invention preferably comprises stimulation of the target component in order to generate, at the electrode, a signal whose modulation by the test substance is intended to be detected. Target components, for example ion channels, can be stimulated by various methods, for example by applying a voltage across the membrane, by intracellularly and/or extracellularly acting ligands or by mechanical changes or combinations thereof.

Voltage-controlled ion channels change their conductance as a function of the voltage drop across the membrane. The conductance of voltage-controlled ion channels can be modulated by applying an external voltage, for example a DC or AC voltage. An additional electrode may optionally be used for this purpose as well, for example a patch-camp electrode which is introduced into the cell or is in direct contact with it. The voltage drop can be set to a fixed value in this way.

The target component may also be stimulated by a ligand. There are two mechanisms for ligand-controlled ion channels, namely ionotropic and second-messenger systems. In ionotropic systems, ligand molecules bind directly to the target component and change its characteristics; for example, intracellular calcium ions can affect the conductance of potassium channels. In second-messenger systems, the ligand molecules bind to a receptor which affects the ion channel only via a signal cascade.

Of course, these various methods of stimulating the target components may also be combined in order to provide an effective system for measuring the influence of the change in ambient parameters, for example test substances, on a target component in the cell.

Another aspect of the present invention is a bioelectronic device comprising a cell which contains a target component, a potential-sensitive electrode, the cell being immobilized on the potential-sensitive electrode and the target component being capable of producing a measurable signal at the electrode, and a medium with a salt concentration of $\leq 100$ mmol/l.

The bioelectronic device may be used for the measurement of signals due to the target component at the potential-sensitive electrode. Analysis is preferably carried out on individual cells, it being possible to determine the location or/and other characteristics, for example the properties of an ion channel on an individual cell. The bioelectronic device is therefore suitable as a sensor, for example to determine the change in an ambient parameter as a detectable signal at the electrode. In particular, the device is suitable for determining whether a substance is a modulator, for example an activator or inhibitor, of the target component of the cell.

A further aspect of the present invention relates to a method of locating a cell on an array comprising the steps of:
(a) preparing a cell, immobilized on an extracellular potential-sensitive electrode, which contains the target component,
(b) measuring a signal at the electrode Induced by the presence of a cell in a medium which has a salt concentration $\leq 100$ mmol/l, and
(c) locating the position of the immobilized cell by means of the measurement in (b).

In this method, the array preferably comprises a plurality of extracellular potential-sensitive electrodes. Favourable site-specific measurement can be carried out by means of this method.

Figure 1:
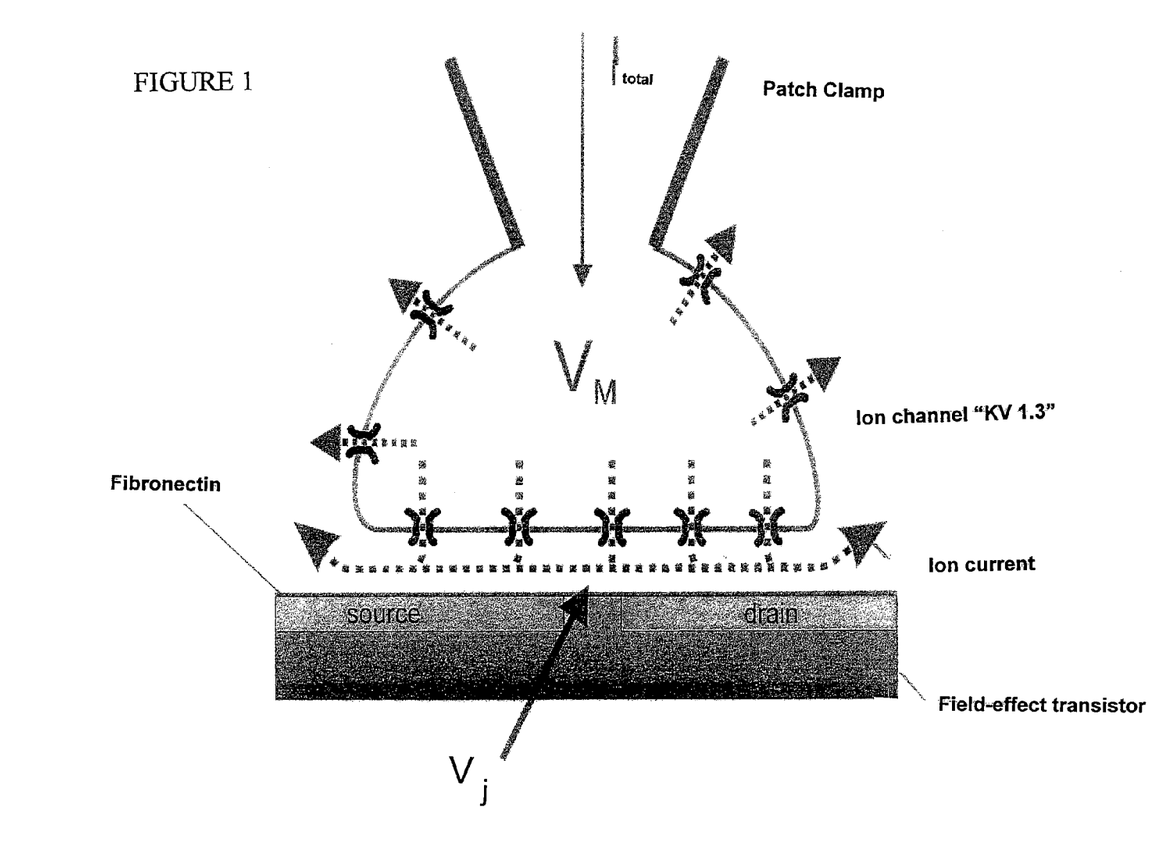
FIG. 1: Shows a cell which is immobilized on a field-effect transistor with a drain, a source and a gate, and which contains an ion channel in its membrane, for example the KVb1.3 potassium channel. The surface of the electrode is coated with fibronectin. A patch electrode for setting a defined potential is furthermore introduced into the cell.

Two preferred embodiments of the present invention will be explained in more detail below. The first embodiment is represented in FIG. 1 and shows a cell which is immobilized on a field-effect transistor with a drain, a source and a gate, and which contains an ion channel in its membrane, for example the KV1.3 potassium channel. The surface of the electrode is coated with fibronectin. A patch electrode for setting a defined potential is furthermore introduced into the cell. In this embodiment, the channels located in the cell membrane are stimulated by applying a DC voltage. The voltage drop $V_j$ in the potential-sensitive electrode is given by the specific conductivity of the adhered membrane $g_{jm}$ and by the specific conductivity of the gap $g_j$:

$$V_j = \frac{g_{jm}}{g_{jm} + g_j}(V_m - V_o)$$

where $V_m$ is the intracellular voltage and $V_o$ is the Nernst potential of the cell.

Figure 2:
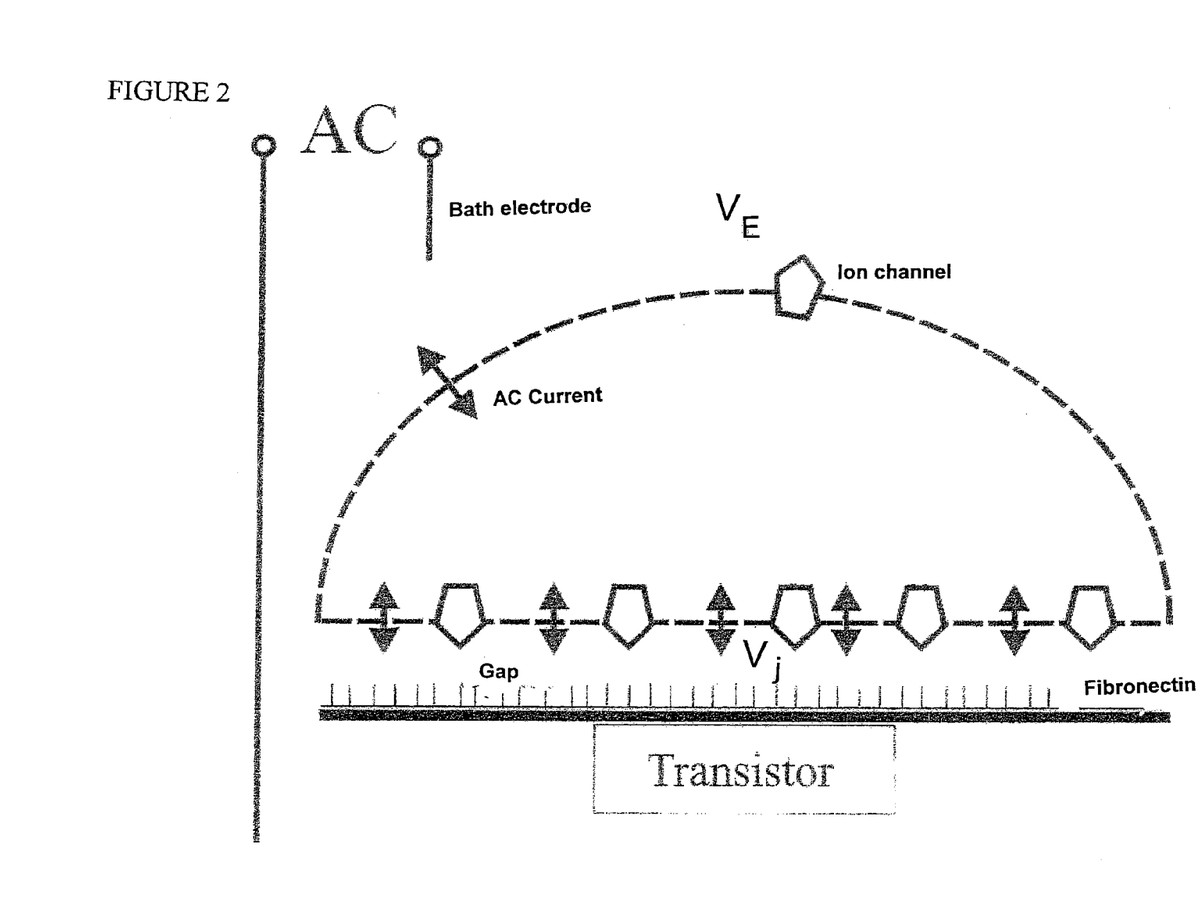
FIG. 2: Demonstrates an embodiment of the invention relating to the measurement of target components, for example closed of open ion channels, when AC voltage is applied.

The second embodiment relates to the measurement of target components, for example closed or open ion channels, when AC voltage is applied. This embodiment is shown in FIG. 2.

The ratio between the stimulating voltage $V_E$ (in the medium) and the voltage in the gap $V_j$ measured by the transistor can be determined by the following formula:

$$h = \frac{V_f}{V_E} = \frac{1 + i\omega \tau_j h_\infty}{1 + i\omega \tau_j},$$

$$\text{where } h_\infty = \frac{c_m}{c_m + (1+\beta)c_{ox}}$$

$$\text{and } \tau_j = \frac{c_m + (1+\beta)c_{ox}}{g_m + (1+\beta)g_j}$$

$\tau_j$ is the characteristic time constant of the transfer function $V_j/V_E$,
$h_\infty$ is the ratio $V_j/V_E$ in the limiting case of high frequencies,
$\omega$ is the frequency $*2*\pi$,
$c_m$ is the specific membrane capacitance,
$c_{ox}$ is the specific oxide capacitance of the chip surface,
$\beta$ is the surface-area ratio of the upper to the adhered membrane,
$g_m$ is the specific membrane conductivity,
$g_j$ is the specific conductivity in the gap.

If $g_j$ is of the order of $g_m$, then a change in the membrane conductance (for example due to the opening of ligand-controlled channels in the cell membrane) can be measured in the phase and in the amplitude of the transfer function. A reduction in $g_j$ due to the new electrolyte composition achieves this purpose. In the previous electrolyte composition, the membrane conductance is negligible and a change in it cannot be measured in the transfer function.

The device and the method are suitable for determining a variation in ambient parameters as a detectable signal at the electrode. In particular, the method is suitable for determining whether a test substance can activate or inhibit the receptor component of an ion-channel/receptor system. The receptor component may be a pharmaceutically relevant target molecule. For examples the effect of test substances on the release of neurotransmitters may be studied.

In another embodiment, the method is suitable for detecting the presence or amount of a substance which acts as an effector on the receptor component.

Figure 3:
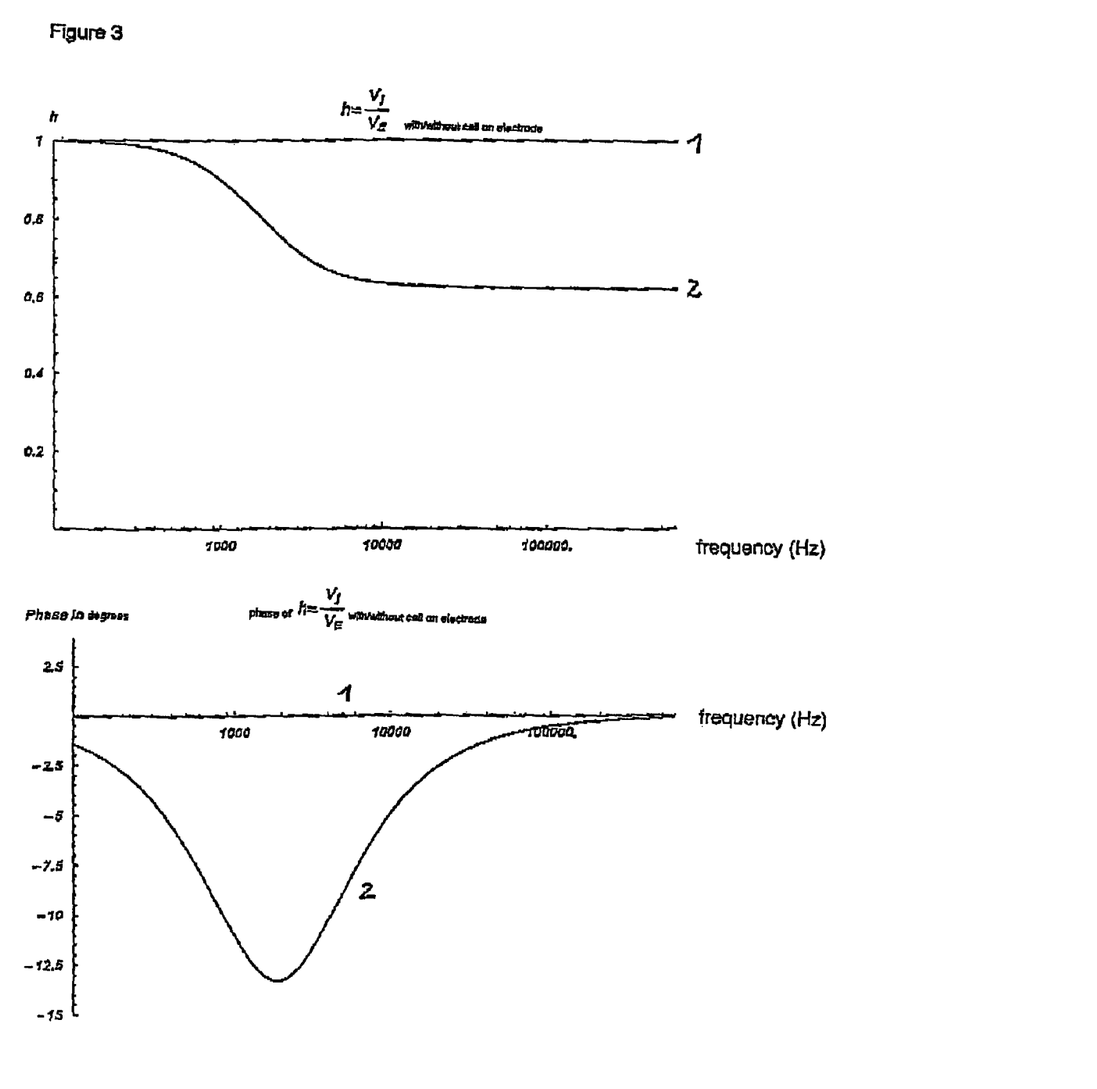
FIG. 3: The transfer function $V_j$ $V_E$ is used to locate immobilized cells when an electrode array is used. One individual cell is preferably tested per electrode. (A): (1): shows the profile of h without a cell; (2) shows the profile of h with a cell. (B): (1): the phase of h without a cell is shown as a curve; (2) the phase of h with a cell is shown as a curve.

When an electrode array is used, the transfer function $V_j/V_E$ can be used to locate individual immobilized cells (see FIG. 3). In this case, one individual cell is preferably tested per electrode. In FIG. 3A, curve (1) shows the profile
of h without a cell, while curve (2) shows the profile of h with a cell. In FIG. 3B, the phase of h without a cell is shown as curve (1) and with a cell as curve (2).

The invention will furthermore be explained by the following examples.
1. Materials and Methods
1.1 Plasmids and Cells
HEK293 cells were stably transfected by the calcium phosphate method with a plasmid, which was obtained by cloning a nucleic acid coding for the human KV1.3 potassium channel in the vector pcDNA3 (Invitrogen).
1.2 Cell Culture on the Substrate
The transfected cells were applied to a fibronectin-coated silicon chip with 62 field-effect transistors. After 1 day in culture, the nutrient liquid was replaced by a physiological extracellular solution (135 mM NaCl, 5 mM KCl, 1.8 mM $CaCl_2$, 1 mM $MgCl_2$, osmolality balanced to 340 mOsmol/kg with glucose, pH 7.4). Cells may optionally be provided with patch-clamp electrodes.

Figure 4A:
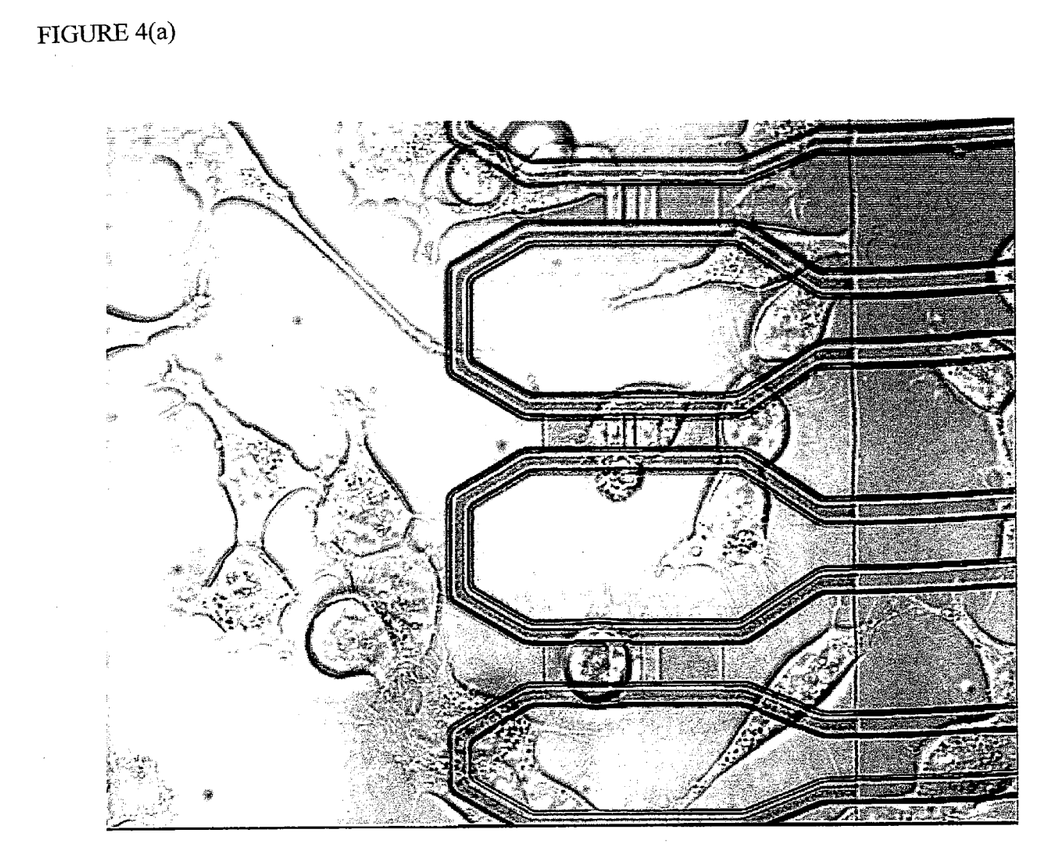
FIG. 4: Shows a transfected cell which has adhered to the gate of an ESOFET (electrolyte oxide silicon field-effect transistor), before (A) and after (B) the measurement by a patch clamp.
Figure 4B:
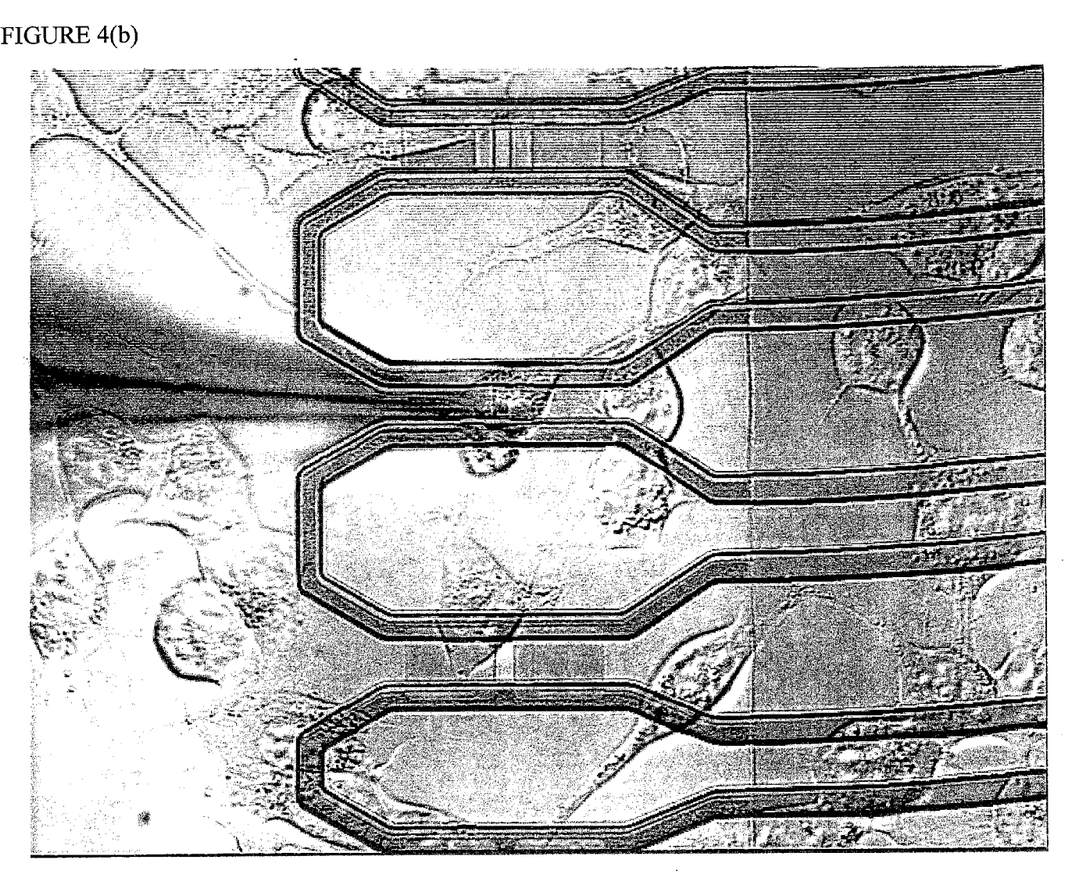

FIG. 4 shows a transfected cell which has adhered to the gate of an EOSFET (electrolyte oxide silicon field-effect transistor), before (A) and after (B) the measurement by a patch clamp.

Figure 5:
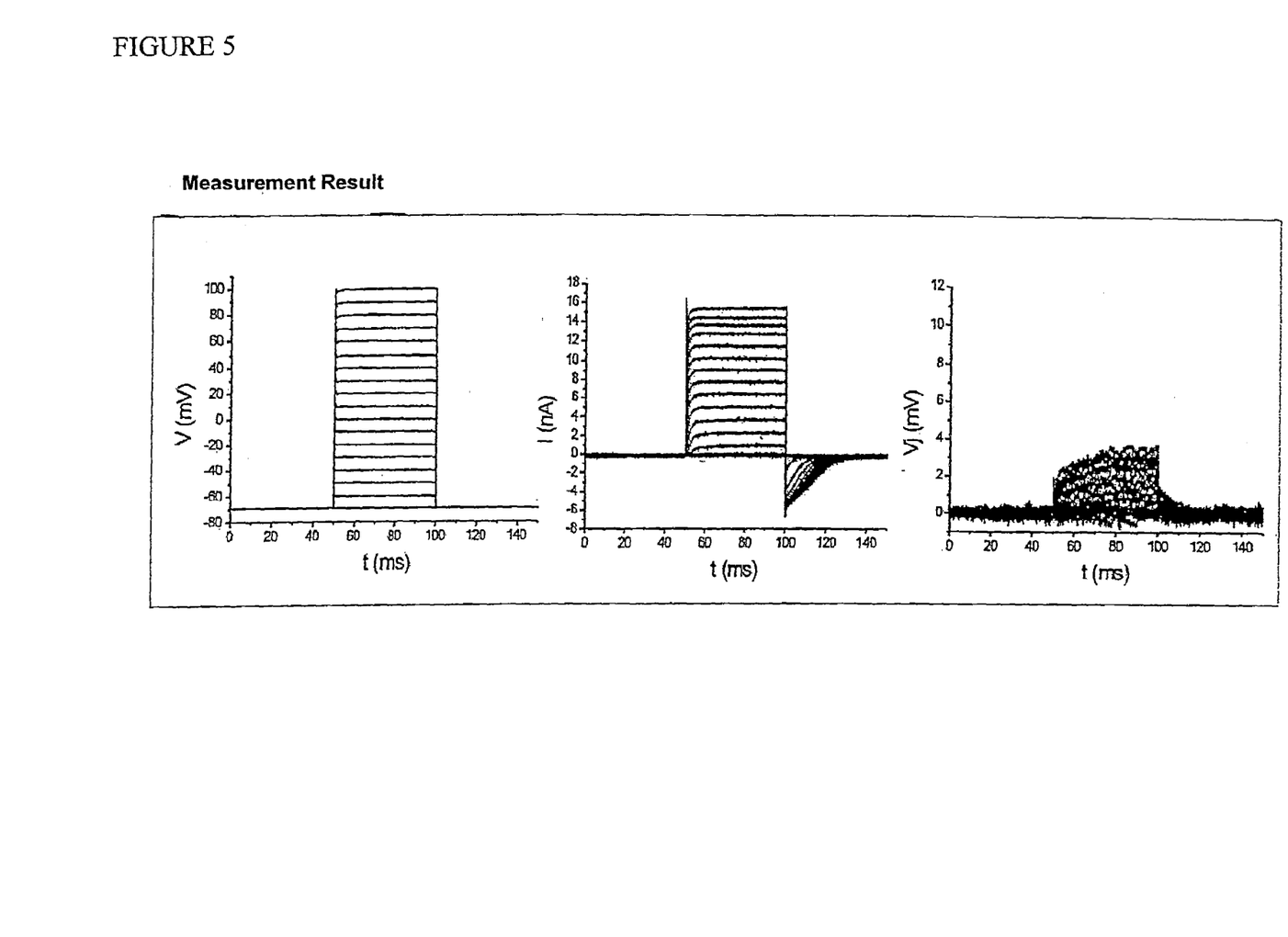
FIG. 5: Shows the effect of physiological extracellular solution. The voltage in the cell V, the current in the cell 1 and the gate voltage drop in the gap $V_j$ are plotted against time. The pulse length is 50 ms. The measurements are carried out in the voltage-clamp mode. The current exhibits the typical time dependency of the KV1.3 channel.

FIG. 5 shows the effect of physiological extracellular solution. The voltage in the cell V, the current in the cell I and the gate voltage drop in the gap $V_j$ are plotted against time. The pulse length is 50 ms. The measurements are carried out in the voltage-clamp mode. The current exhibits the typical time dependency of the KV1.3 channel.

Figure 6:
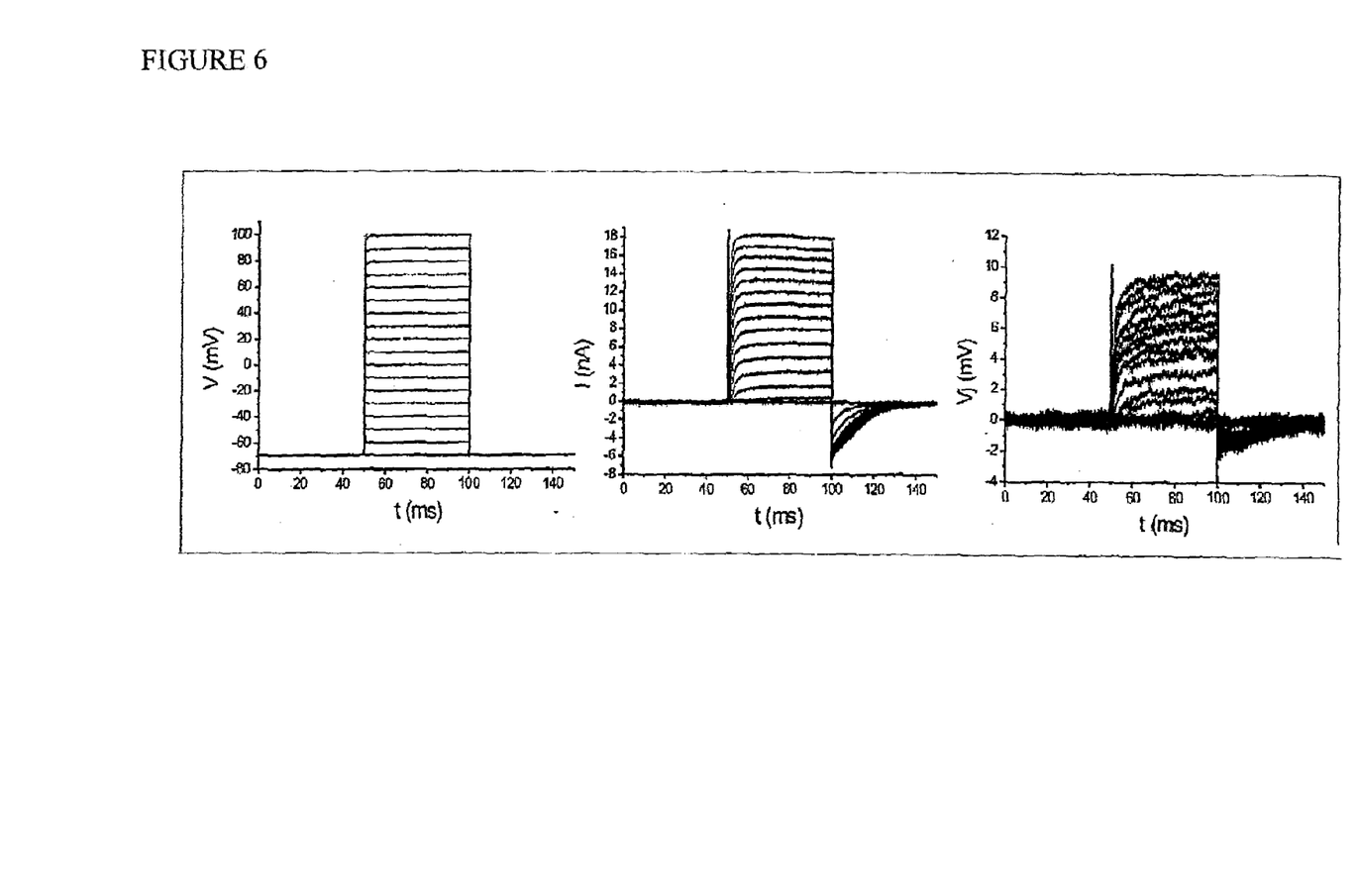
FIG. 6: The measurement when the extracellular solution is replaced by an NaCl-free solution (0 mM NaCl. 5 mM KCl. 1.8 mM CaCl$_2$, osmolality balanced to 340 mOsmol/kg with glucose, pH 7.4).

If the physiological extracellular solution is now replaced by an NaCl-free solution (0 mM NaCl, 5 mM KCl, 1.8 mM $CaCl_2$, 1 mM $MgCl_2$, osmolality balanced to 340 mOsmol/kg with glucose, pH 7.4), then this leads to the measurement shown in FIG. 6. The replacement of the solution leads to a significant improvement in the signal-to-noise ratio due to a signal increase by the factor 4. The behaviour of the ion channels is not affected by the change of solution (both maximum current and the time dependency remain unaltered), and the cells suffer no observable damage.

Figure 7A:
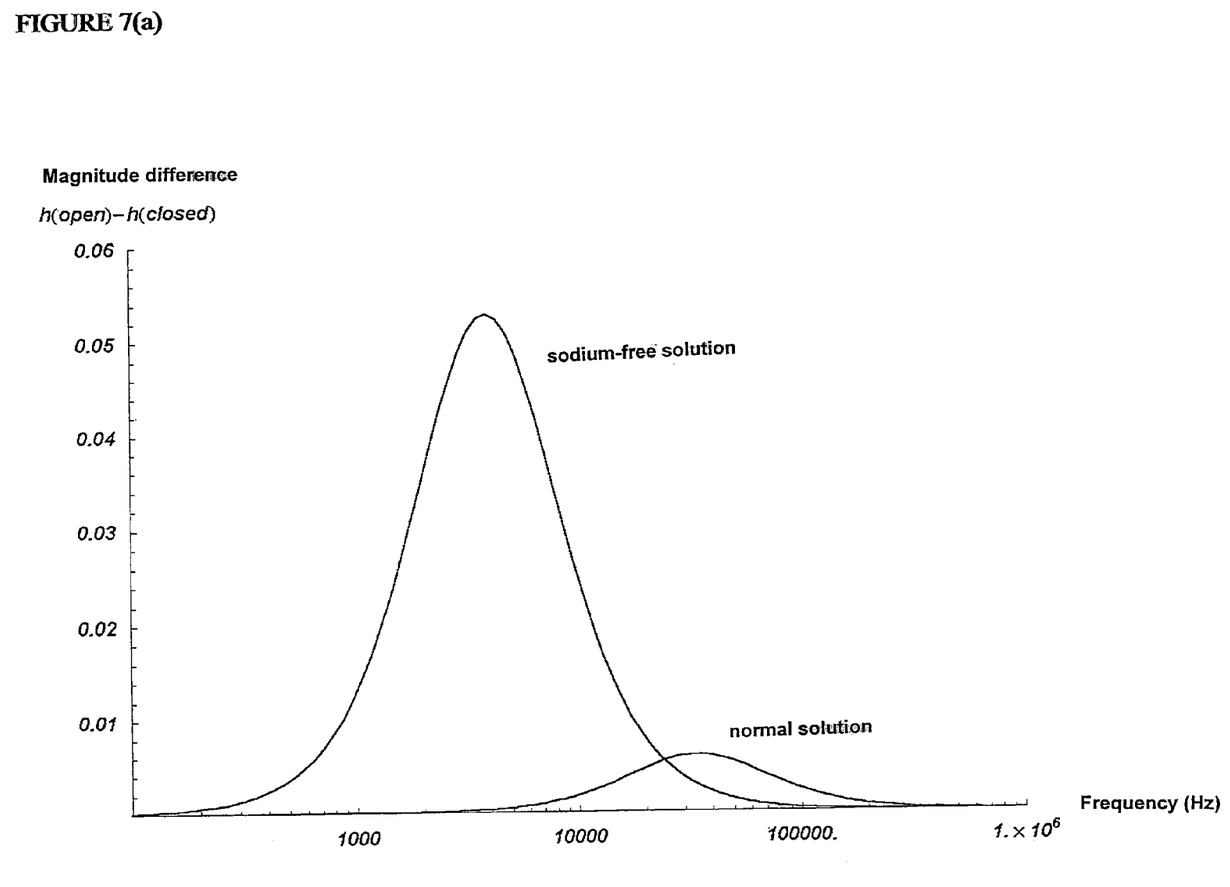
FIG. 7: Shows the difference between the measurements with normal solutions and sodium-free solutions after stimulation by AC voltage.
Figure 7B:
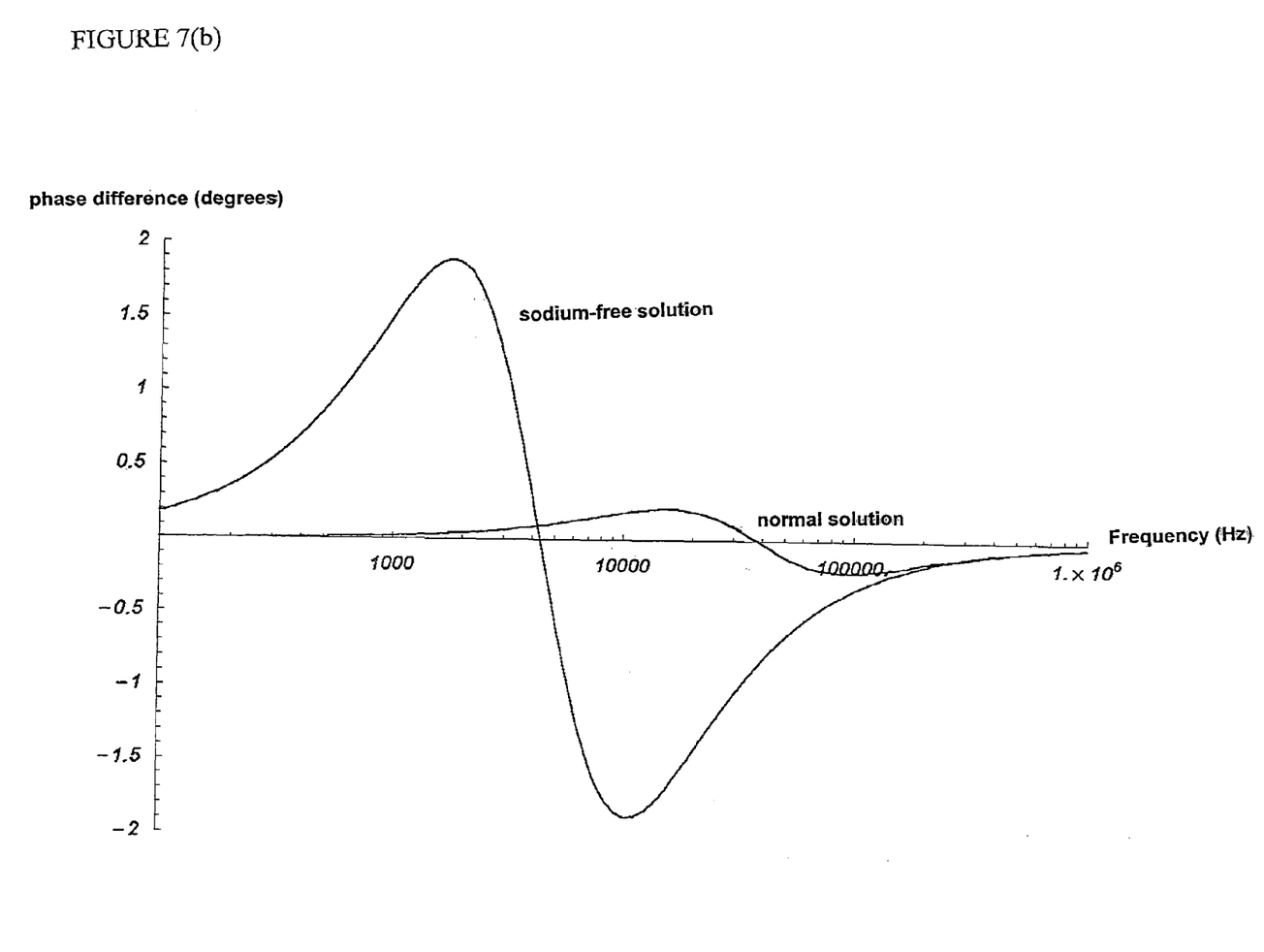

The difference between the measurements with normal solutions and sodium-free solutions after stimulation by AC voltage is shown in FIG. 7.

The invention claimed is:

1. A method for determining whether a substance is a modulator of an ion-channel/receptor system containing a ligand controlled or mechanically controlled ion channel, comprising the steps of:
   (a) preparing a cell, which contains the ion-channel/receptor system, wherein the cell is immobilized on an extracellular potential-sensitive electrode,
   (b) bringing a substance to be tested in contact with the cell, in a medium which has a total salt concentration of $\leq 100$ mmol/L,
   (c) stimulating the ion-channel/receptor system,
   (d) measuring a signal at the electrode due to the ion-channel/receptor system, and
   (e) determining the effect of the substance to be tested on the measurement signal.

2. The method according to claim 1, characterized in that the ion channel is a potassium channel.

3. The method according to claim 1, characterized in that the ion-channel/receptor system contains an NMDA, GABA, AMPA or acetylcholine receptor.

4. The method according to claim 1, characterized in that the stimulation of the ion-channel/receptor system comprises, chemical stimulation or mechanical stimulation.

5. The method according to claim 1, characterized in that the potential-sensitive extracellular electrode is arranged on a chip.

6. The method according to claim 1, characterized in that an array comprising a multiplicity of cells immobilized on different electrodes is prepared, and a multiplicity of substances are tested.

* * * * *